United States Patent [19]

Frisch

[11] Patent Number: 5,866,550
[45] Date of Patent: Feb. 2, 1999

[54] METHOD OF INHIBITING REPLICATION OF HYPERPROLIFERATIVE CELLS USING A NUCLEIC ACID ENCODING EIA

[75] Inventor: Steven M. Frisch, Del Mar, Calif.

[73] Assignee: La Jolla Cancer Research Foundation, La Jolla, Calif.

[21] Appl. No.: 473,399

[22] Filed: Jun. 6, 1995

Related U.S. Application Data

[63] Continuation of Ser. No. 960,112, Oct. 13, 1992, Pat. No. 5,516,631.
[51] Int. Cl.$^6$ .............................. A68K 48/00; C12N 15/00
[52] U.S. Cl. ............................... 514/44; 424/93.2; 935/62
[58] Field of Search ................................ 514/44; 424/93.2

[56] References Cited

U.S. PATENT DOCUMENTS 5,641,484 6/1997 Hung et al. .
5,643,567 7/1997 Hung et al. .
5,651,964 7/1997 Hung et al. .

FOREIGN PATENT DOCUMENTS

WO 94/18992  9/1994  WIPO .

OTHER PUBLICATIONS

Bio World Today (Jun. 10, 1996) vol. 7, No. 113, pp. 1–2, "RGene Signs . . . ".
Mena et al (1996) Nature Med. 2, 974–975.
Roth et al (1996) Nature Med. 2, 985–991.
Xu et al (1996) Cancer Res. 56, 2245–2249.
Yu et al (1995) Oncogene 11, 1383–1388.
Mulligan (1993) Science 260, 926–932.
Muenchau et al (1990) Virol. 176, 262–265.
O'Reilly et al (1996) Nature Med. 2, 689–692.
Mymryk (1996) Oncogene 13, 1–9.
Vieweg et al (1995) Cancer Invest. 13, 193–201.
Frisch et al (1990) Oncogene 5, 75–83.
Van Beusecheum et al (1990) J. Exp. Med. 172, 729–736.
Flint et al., "Adenovirus E1A Protein Paradigm Viral Transactivator", *Ann. Rev. Gen.* 23:141–161 (1989).
Ruley, H.E., "Adenovirus early region 1A enables viral and cellular transforming genes to transform primary cells in culture", *Nature* 304:602–606 (1983).
Howe et al., "Retinoblastoma growth suppressor and a 300–kDa protein appear to regulate cellular DNA synthesis", *Proc. Natl. Acad. Sci.* 87:5883–5887 (1990).
Graham et al., "Characteristics of a Human Cell Line Transformed by DNA from Human Adenovirus Type 5", *J. Gen. Virol.* 36:59–72 (1977).
Byrd et al., "Malignant transformation of human embryo retinoblasts by cloned adenovirus 12 DNA", *Nature* 298:69–71 (1982).

Huang et al., "Suppression of the Neoplastic Phenotype by Replacement of the RB Gene in Human Cancer Cells," *Science* 242:1563–1566 (1988).
Chen et al., "Genetic Mechanisms of Tumor Suppression by the Human p53 Gene", *Science* 250:1576–1580 (1990).
Walker et al., "E1A oncogene induction of cytolytic susceptibility eliminates sarcoma cell tumorigenicity", *Proc. Natl. Acad. Sci. USA* 88:6491–6495 (1991).
Yu et al., "Adenovirus Type 5 E1A Gene Products Act as Transformation Suppressors of the neu Oncogene", *Molec. Cell. Biol.* 11:1745–1750 (1991).
Miller et al., "Improved Retroviral Vectors for Gene Transfer and Expression", *Biotechniques* 7:980–990 (1989).
Brunet et al., "Concentration Dependence of Transcriptional Transactivation in Inducible E1A–Containing Human Cells", *Molec. Cell. Biol.* 8:4799–4807 (1988).
Yu et al., "Reexpression of neu–encoded Oncoprotein Counteracts the Tumor–suppressing but not the Metastasis–suppressing Function of E1A." *Cancer Research.*, 53:5784–5790 (1993).
Frisch, Steven M., "Antioncogenic effect of adenovirus E1A in human tumor cells." *Proc. Natl. Acad. Sci.*, 88:9077–9081 (1991).
Mymryk, Joe S., "Tumor suppressive properties of the adenovirus 5 E1A oncogene." *Oncogene*, 13:1–9 (1996).
Minna and Gazdar, "Translational research comes of age." *Nature Medicine*, 2:974–975 (1996).
Roth et al., "Retrovirus–mediated wild–type p53 gene transfer to tumors of patients with lung cancer." *Nature Medicine*, 2:985–991 (1996).
Xu et al., "Enhanced Tumor Suppressor Gene Therapy via Replication–deficient Adenovirus Vectors Expressing an N–Terminal Truncated Retinoblastoma Protein." *Cancer Research*, 56:2245–2249 (1996).
Yu et al., "Lipsome–mediated in vivo E1A gene transfer suppressed dissemination of ovarian cancer cells that overexpress HER–2/neu." *Oncogene*, 11:1383–1388 (1995).
Shrine, Jim, "Rgene Signs $25M Agreement For Tumor Suppressor Product." *BioWorld Today*, 7:1–2 (1995).

*Primary Examiner*—Deborah Crouch
*Attorney, Agent, or Firm*—Campbell & Flores LLP

[57] ABSTRACT

This invention relates to methods for converting a pathologic hyperproliferative human cell to its non-malignant phenotype. The method comprises introducing into the cell a nucleic acid encoding a polypeptide having adenovirus E1A activity and growing the cell under conditions such that the polypeptide is produced. This invention also relates to a method of converting a population of pathologic hyperproliferative cells in a subject to a non-hyperproliferative state by expressing, in some but not all of the hyperproliferative cells, an isolated nucleic acid sequence encoding a polypeptide having adenovirus E1A activity. In a further aspect, the invention relates to promoting differentiation of pathologically hyperproliferative cells.

12 Claims, 8 Drawing Sheets

| Cell line | Cells injected, no. | Incubation time, days | Average tumor mass, g | SD |
|---|---|---|---|---|
| HT1080 | 6 × 10⁶ | 17 | 2.2 | 0.62 |
| p2AHT2a | 6 × 10⁶ | 17 | 0.04 | 0.04 |
| HT1080 | 2 × 10⁶ | 17 | 1.2 | 0.3 |
| p1Aneo15 | 2 × 10⁶ | 17 | 0.25* | 0.3 |
| p1Aneo16 | 2 × 10⁶ | 17 | 0.0 | 0 |
| A2058 | 1 × 10⁷ | 18 | 1.2 | 0.3 |
| 1A58c8-1 | 1 × 10⁷ | 18 | 0.0 | 0 |
| 1A58c11-1 | 1 × 10⁷ | 18 | 0.0 | 0 |
| HeLa | 1 × 10⁶ | 15 | 0.4 | 0.1 |
| Medg 28 | 1 × 10⁶ | 15 | 0.1 | 0.03 |

FIG. 4

```
GGACTGAAAA ATG AGA CAT ATT ATC TGC CAC GGA GGT GTT ATT ACC GAA    48
           Met Arg His Ile Ile Cys His Gly Gly Val Ile Thr Glu
            1               5                      10

GAA ATG GCC GCC AGT CTT TTG GAC CAG CTG ATC GAA GAG GTA CTG GCT    96
Glu Met Ala Ala Ser Leu Leu Asp Gln Leu Ile Glu Glu Val Leu Ala
         15                  20                  25

GAT AAT CTT CCA CCT CCT AGC CAT TTT GAA CCA CCT ACC CTT CAC GAA   144
Asp Asn Leu Pro Pro Pro Ser His Phe Glu Pro Pro Thr Leu His Glu
         30                  35                  40          45

CTG TAT GAT TTA GAC GTG ACG GCC CCC GAA GAT CCC AAC GAG GAG GCG   192
Leu Tyr Asp Leu Asp Val Thr Ala Pro Glu Asp Pro Asn Glu Glu Ala
         50                  55                  60

GTT TCG CAG ATT TTT CCC GAC TCT GTA ATG TTG GCG GTG CAG GAA GGG   240
Val Ser Gln Ile Phe Pro Asp Ser Val Met Leu Ala Val Gln Glu Gly
         65                  70                  75

ATT GAC TTA CTC ACT TTT CCG CCG CCC GCG GGT TCT CCG GAG CCG CCT   288
Ile Asp Leu Leu Thr Phe Pro Pro Pro Ala Pro Gly Ser Pro Glu Pro Pro
         80                  85                  90
```

FIG.5A

```
CAC CTT TCC CGG CAG CCC GAG CAG CCG GAG CAG AGA GCC TTG GGT CCG      336
His Leu Ser Arg Gln Pro Glu Gln Pro Glu Gln Arg Ala Leu Gly Pro
 95                     100                 105

GTT TCT ATG CCA AAC CTT GTA CCG GAG GTG ATC GAT CTT ACC TGC CAC      384
Val Ser Met Pro Asn Leu Val Pro Glu Val Ile Asp Leu Thr Cys His
110                     115                 120                 125

GAG GCT GGC TTT CCA CCC AGT GAC GAC GAG GAT GAA GAG GGT              426
Glu Ala Gly Phe Pro Pro Ser Asp Asp Glu Asp Glu Glu Gly
                130                 135

GAGGAGTTTG TGTTAGATTA TGTGGAGCAC CCCGGGCACG GTTGCAGGTC TTGTCATTAT    486
GluGluPheV alLeuAspTy rValGluHis ProGlyHisG lyCysArgSe rCysHisTyr

CACCGGAGGA ATACGGGGGA CCCAGATATT ATGTGTTCGC TTTGCTATAT GAGGACCTGT    546
HisArgArgA snThrGlyAs pProAspIle MetCysSerL euCysTyrMe tArgThrCys

GGCATGTTTG TCTACAGTAA GTGAAAAATTA TGGGCAGTGG GTGATAGAGT GGTGGGTTTG   606
GlyMetPheV alTyrSer

GTGTGGTAAT TTTTTTTTTA ATTTTTACAG TTTTGTGGTT TAAAGAATTT TGTATTGTGA    666

TTTTTTTAAA AGGT CCT GTG TCT GAA CCT GAG CCC GAG CCA GAA              716
            Pro Val Ser Glu Pro Glu Pro Glu Pro Glu
            140                 145                 150
```

FIG.5B

```
CCG GAG CCT GCA AGA CCT ACC CGC CGT CCT AAA ATG GCG CCT GCT ATC    764
Pro Glu Pro Ala Arg Pro Thr Arg Arg Pro Lys Met Ala Pro Ala Ile
            155                 160                 165

CTG AGA CGC ACA TCA CCT GTG TCT AGA GAA TGC AAT AGT AGT ACG        812
Leu Arg Arg Thr Ser Pro Val Ser Arg Glu Cys Asn Ser Ser Thr
            170                 175                 180

GAT AGC TGT GAC TCC GGT CCT TCT AAC ACA CCT CCT GAG ATA CAC CCG    860
Asp Ser Cys Asp Ser Gly Pro Ser Asn Thr Pro Pro Glu Ile His Pro
            185                 190                 195

GTG GTC CCG CTG TGC CCC ATT AAA CCA GTT GCC GTG AGA GTT GGT GGG    908
Val Val Pro Leu Cys Pro Ile Lys Pro Val Ala Val Arg Val Gly Gly
200                 205                 210                 215

CGT CGC CAG GCT GTG GAA TGT ATC GAG GAC TTG CTT AAC GAG CCT GGG    956
Arg Arg Gln Ala Val Glu Cys Ile Glu Asp Leu Leu Asn Glu Pro Gly
            220                 225                 230

CAA CCT TTG GAC TTG AGC TGT AAA CGC CCC AGG CCATAAGGTG T          1000
Gln Pro Leu Asp Leu Ser Cys Lys Arg Pro Arg Pro
            235                 240
```

METHOD OF INHIBITING REPLICATION OF HYPERPROLIFERATIVE CELLS USING A NUCLEIC ACID ENCODING EIA

This application is a continuation of application Ser. No. 07/960,112, filed Oct. 13, 1992 now U.S. Pat. No. 5,516,613 issued May 14, 1996.

The present invention was made with support in part from a National Institutes of Health Grant 7-R29-GM44573-03 and an Institutional Support Grant Account No. 1-17071-6460. The United States Government may have certain rights in the invention.

BACKGROUND OF THE INVENTION

Adenovirus is a large DNA virus whose natural host is human cells. Virtually every adult has been infected with adenovirus at some time, the major effect being cold-like symptoms. Adenovirus is referred to as a "DNA tumor virus" purely because of its oncogenic effect in rodents. Expression of the adenovirus genome occurs in two stages. First, the early gene products are expressed which encode the E1A and E1B genes. These products are necessary for expression of the late gene products. Late gene products encode proteins necessary for replication as well as the viral structural proteins.

The proteins encoded by the E1A gene of adenovirus have been studied primarily from two points of view. First, the 243 amino acid and 289 amino acid forms of E1A (arising from alternative splicing of the precursor RNA such that the 243 amino acid protein is a subset of the 289 amino acid protein) are both transcriptional regulatory proteins, J. Flint, T. Shenk, *Ann. Rev. Gen.* 23:141–161 (1989). Secondly, these proteins facilitate the oncogenic transformation of certain rodent cells by other oncogenes, H. E. Ruley, *Nature* 304:602–606 (1983), and, as such E1A is generally classified as an oncogene. The interactions of E1A proteins with various defined cellular proteins are believed to mediate its oncogenic effects in rodent cells, J. M. Howe, et al., *Proc. Natl. Acad. Sci.* 87:5883–5887 (1990).

In human cells, E1A does not appear to cooperate with other oncogenes to transform cell lines, however, mild tumorigenic effects have been reported in only two instances. For example, embryonic kidney, F. Graham, J. Smiley, W. Russell, R. Nairn, *J. Gen. Virol.* 36:59–72 (1977), and embryonic retinoblast cell lines, P. J. Byrd, K. W. Brown, P. H. Gallimore, *Nature* 298:67–71 (1982), stably expressing E1A are weakly tumorigenic when injected into mice. Moreover, these transformants arise very rarely after cotransfection of E1A with another oncogene.

The normal and transformed phenotypes of a cell are thought to be maintained by a balance of activities encoded by oncogenes and antioncogenes (tumor suppressor genes). The absence of functional tumor suppressor gene products contributes to carcinogenesis. Conversely, replacement or overexpression of these products promises to be useful in controlling tumor cell growth. Only a limited number of tumor suppressor genes have been characterized at present, notably, retinoblastoma protein, Huang et al., *Science* 24:1563–1566 (1988), and p53, Chen et al., *Science* 250:1566–1570 (1990). However, when reintroduced into tumor cells, both of these gene products simply kill the cells.

Two reports in the literature claim tumor suppression effects of E1A, but both of these effects arose from epiphenomena not related to the growth controlling effects of E1A expression. Rat sarcoma cells stably transfected with E1A are less tumorigenic in nude rats than their untransfected counterparts (T. A. Walker, B. A. Wilson, A. M. Lewis, J. L. Cook, *Proc. Natl. Acad. Sci.*, 88:6491–6495 (1991). Decreased tumorigenicity of E1A-expressing cells resulted from sensitization of these cells to cytolysis by natural killer cells and these cells were still tumorigenic in nude mice. The second report (D. Yu, K. Scorsone, M. C. Huang *Molec. Cell Biol.* 11:1745–1750 (1991) showed that E1A prevented an oncogene known as neu from transforming the mouse cell line 3T3. E1A accomplished this solely by inhibiting the expression of neu at the transcriptional level. 3T3 cells transfected with a chimeric neu gene that utilized an E1A-resistant gene promoter were still transformed by neu even in the presence of E1A. The use of E1A to suppress tumor proliferation in the manner implied by the observations above would require E1A expression in all of the cells in the tumor. This requirement poses extreme practical limitations on the use of tumor suppressor genes for therapy since the technology does not exist to introduce a desired gene into 100% of the cell population. In light of these drawbacks, strategies for inhibiting the uncontrolled replication of hyperproliferative cells using tumor suppressor genes have not yet emerged.

Thus, there exists a need to regulate hyperproliferative cell populations through small subpopulations of cells endowed with the ability to dominantly influence their growth. The present invention satisfies this need and provides related advantages as well.

SUMMARY OF THE INVENTION

This invention relates to methods for converting a pathologic hyperproliferative human cell to its non-malignant phenotype. The method comprises introducing into the cell a nucleic acid encoding a polypeptide having adenovirus E1A activity and growing the cell under conditions such that the polypeptide is produced. This invention also relates to a method of inhibiting the growth of a population of pathologic hyperproliferative cells in a subject by expressing, in some but not all of the hyperproliferative cells, an isolated nucleic acid sequence encoding a polypeptide having adenovirus E1A activity. In a further aspect, the invention relates to promoting differentiation of pathologically hyperproliferative cells.

DETAILED DESCRIPTION OF THE INVENTION

The present invention results from the observation that the adenovirus E1A gene unexpectedly influences the phenotype of human tumor cells so as to restore their contact inhibitory properties and promote their differentiation. Stable expression of the adenovirus 5 E1A gene reduces anchorage-independent growth and tumorigenic potential, promotes reorganization, induces flat morphology, and restores contact inhibition in human tumor cell lines. By these criteria, E1A functions as a tumor suppressor gene in this human context. The apparent paradox accorded by the observations of the ability of E1A to transform rodent cells in cooperation with other oncogenes suggests that E1A may be the prototype of a class of growth-regulatory proteins having context-specific transforming and antioncogenic activities.

These unexpected observations provide the basis for this invention, which in one embodiment provides a method for reverse-transforming pathologic hyperproliferative mammalian cells. The cells are contacted with an effective amount of nucleic acid encoding a polypeptide having E1A activity under conditions such that the nucleic acid is introduced into the cell. The cell is then grown under conditions such that the polypeptide is expressed. The method may be practiced in vitro or in vivo.

Provided by this invention is a method for reversing the transformed phenotype of hyperproliferative cells located in pathological tissue by transducing with, for example, retroviral vectors, isolated nucleic acids having E1A activity. Transducing vectors can be introduced by direct injection or other suitable application. Such reverse-transformed cells will arrest growth of neighboring, non-transduced cells.

Alternatively, provided by this invention is a method of reverse-transforming a population of pathologic hyperproliferative cells in a subject which comprises obtaining a suitable sample of cells from the subject, contacting the cells with a suitable retroviral vector containing nucleic acid encoding a polypeptide having E1A activity for a time period for transfection of the nucleic acid into the cell. These cells are then grown under suitable conditions such that the nucleic acid is expressed. The actively expressing cells are then reinfused into the subject.

As used herein, the term "hyperproliferative," as it relates to cells, includes but is not limited to those cells having the capacity for autonomous growth, i.e., existing and reproducing independently of normal regulatory mechanisms.

Hyperproliferative diseases may be categorized as pathogenic, i.e., characterizing or constituting a disease state, or may be categorized as non-pathologic, i.e., a deviation from normal but not associated with a disease state. "Pathologic hyperproliferative" cells occur in disease states characterized by malignant tumor growth including but not limited to breast cancer, sarcomas and other neoplasms, bladder cancer, colon cancer, lung cancer, various leukemias and lymphomas. In addition, the term can be applied to such conditions as thyroid hyperplasia and benign prostatic hypertrophy. Examples of non-pathologic hyperproliferative cells are found, for example, in embryonic tissue, in mammary ductal epithelial cells during development of lactation and also in cells associated with wound repair. Pathologic hyperproliferative cells characteristically exhibit loss of contact inhibition and a decline in their ability to selectively adhere which implies a change in the surface properties of the cell and a further breakdown in intercellular communication.

Figure 5A:
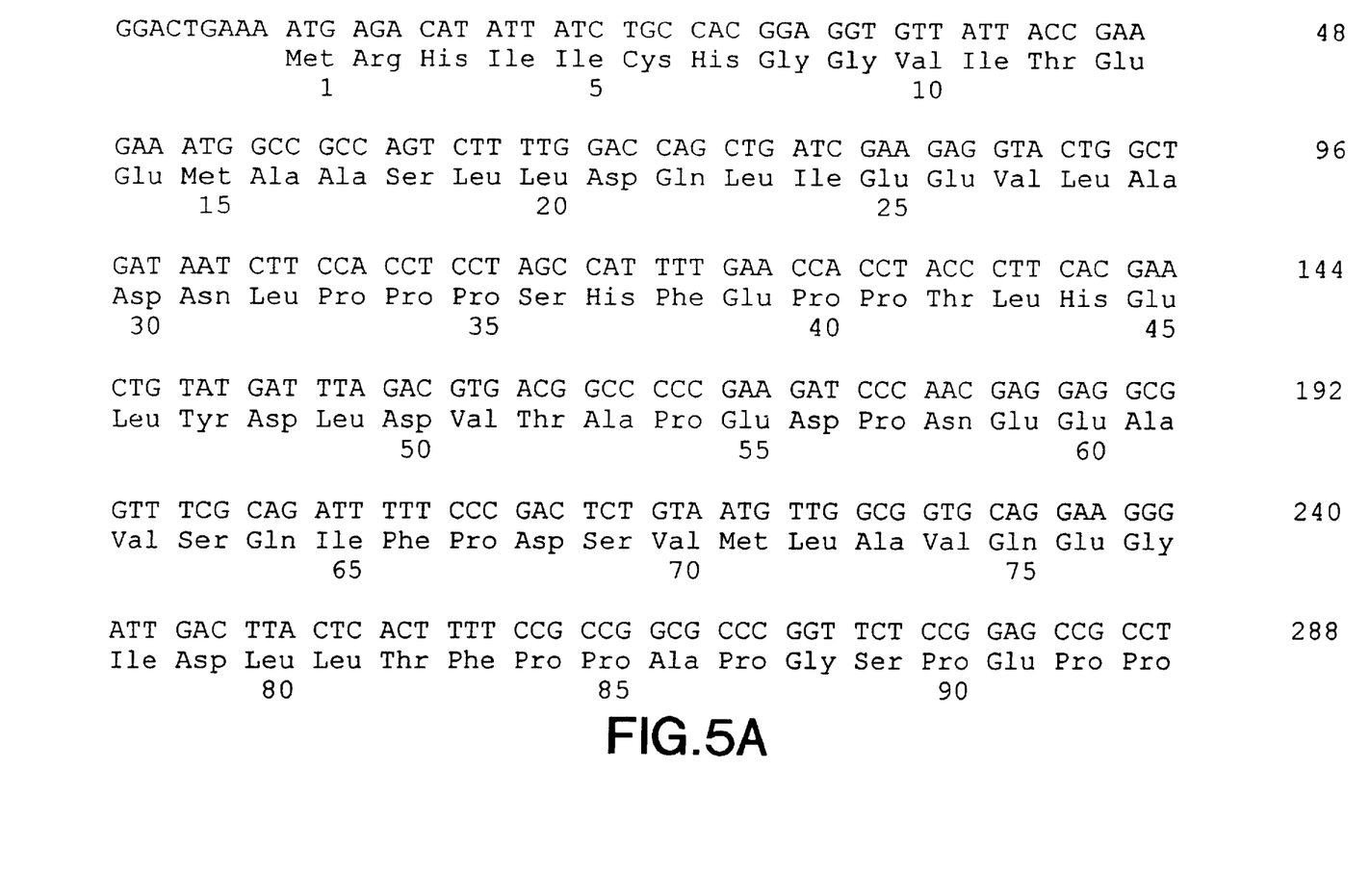
FIGS. 5A to 5C. DNA sequence of E1A coding sequences (cDNA). Bottom line: 243 amino acid sequence. Top line: 289 amino acid sequence.
Figure 5B:
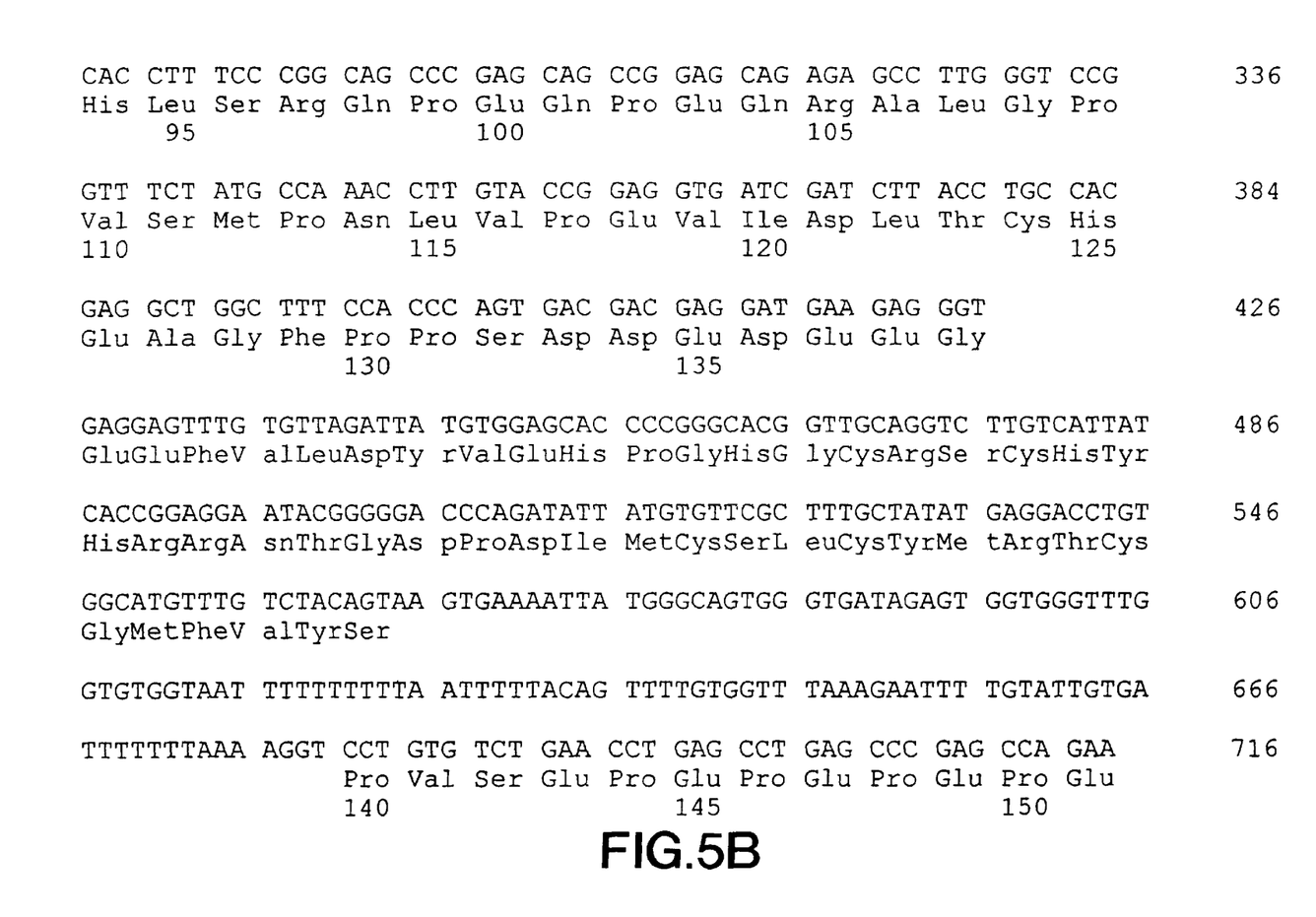
Figure 5C:
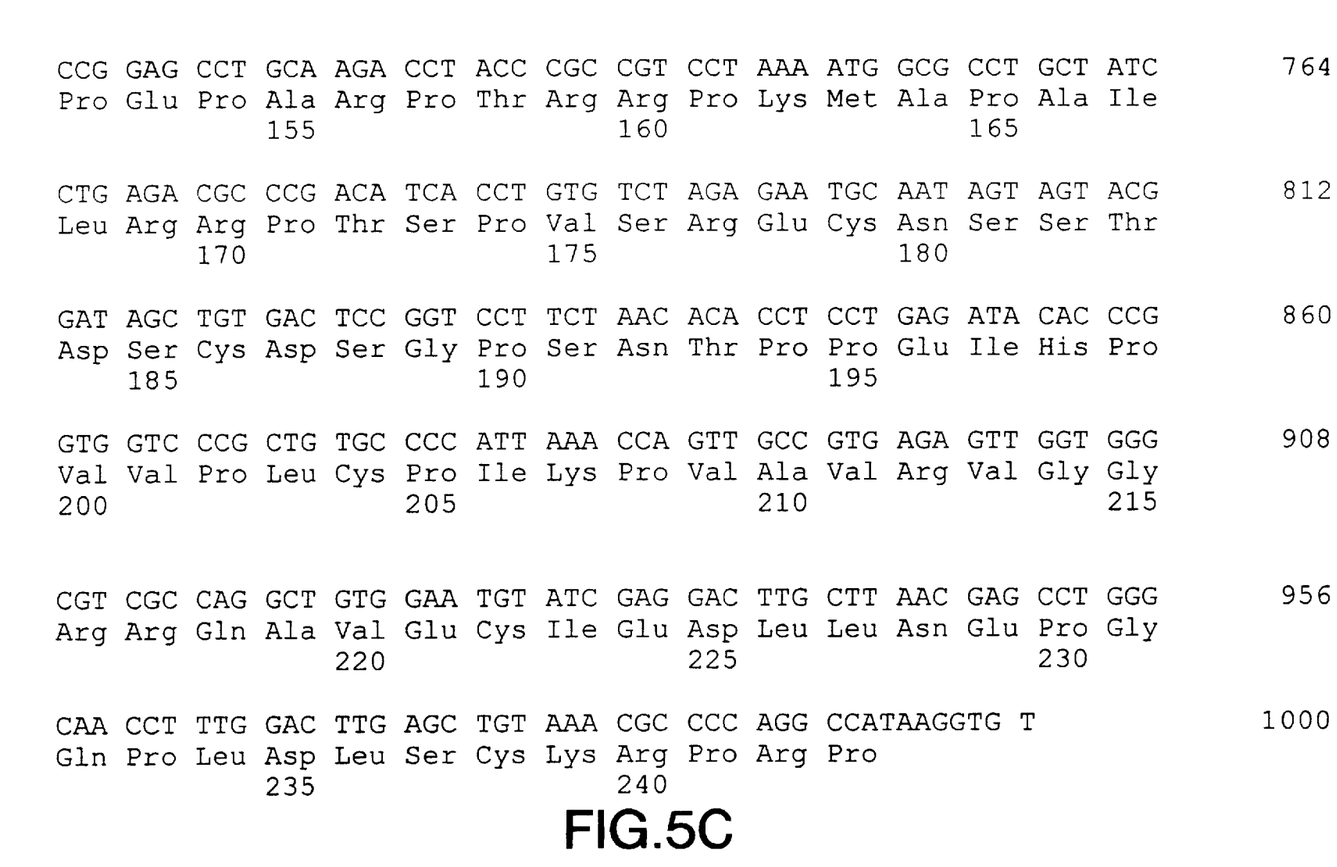

The sequence of E1A is provided in FIG. 5. The E1A gene product has the capacity, when expressed in a malignant cell to convert the phenotype such that the resulting cell is able to inhibit the growth of neighboring tumor cells. Such capacity is herein termed E1A activity. The invention is intended to E1A, its functional subunits and fragments and modifications to the native sequence which retain E1A activity.

As used herein, the term "nucleic acid" means DNA, RNA or cDNA. A "polypeptide having E1A activity" encompasses any amino acid sequence having the biological activity of the adenovirus E1A gene product. In the preferred embodiment of this invention, this amino acid sequence is the 243 amino acid polypeptide product of the adenovirus E1A gene, as provided in FIG. 5. Functional equivalents of the 243 amino acid polypeptide are polypeptides that specifically can also effect promotion of contact inhibition as provided herein.

As used herein, the term "introducing" encompasses any method of inserting an exogenous nucleic acid molecule into a cell and includes, but is not limited to transduction, transfection, microinjection and viral infection of host cells. Methods of carrying out these procedures are well known to those of skill in the art. In the preferred embodiment of this invention, the nucleic acid is introduced into the cell by contacting a cell with a retroviral vector containing the nucleic acid under conditions such that the nucleic acid is inserted into the cell. In the most preferred embodiment of this invention, the virus is a replication-incompetent retrovirus. A replication-incompetent retrovirus is defined as a virus not having the ability to produce viral proteins, precluding spread of the vector in the infected host cells. Examples of such vectors useful for the practice of this invention are well known and readily available to those of skill in the art.

Isolated nucleic acids useful in this invention are those that encode a polypeptide functionally equivalent to a polypeptide encoded by the E1A region of the adenovirus genome. In the preferred embodiment of this invention, the isolated nucleic acid is the adenovirus E1A region. This region is defined by those of skill in the art to be from nucleotide 560 to nucleotide 1542.

This invention also provides a novel form of cancer therapy. Previously, anti-cancer genes or drugs targeted to kill tumor cells were effective in eradicating tumors only if 100% of the cells are exposed to the drug and forced to express the gene. This consistent exposure is seldom, if ever, achieved in vivo. Malignant cells transfected to express the isolated nucleic acids of this invention can dominantly prevent the growth of neighboring tumor cells. Thus, by converting a small fraction of the malignant cells, the tumor can be effectively eradicated or inhibited.

The following examples are intended to illustrate but not limit the invention.

EXAMPLE I

Material and Methods

Stable E1A-expressing cell lines from A2058 melanoma and HT1080 fibrosarcoma cells (ATCC Acession No. CCL121) were constructed using the plasmid p1Aneo as described in Frisch et al., *Oncogene* 5:75–83 (1990), incorporated herein by reference. E1A-expressing HeLa cells, as described in Brunet and Berk, *Mol. Cell. Biol.* 8:4799–4807 (1988), incorporated herein by reference, were obtained from L. Brunet and A. Berk (University of California, Los Angeles). Cells labeled HT1080neo$^r$ and A2058neo$^r$ resulted from transfection with Bluescript plasmid (Stratagene, La Jolla, Calif.) containing the simian virus 40 early enhancer-promoted aph gene (encoding resistance to G418).

Cells were plated at $4 \times 10^4$ (A2058 and derivatives), $3 \times 10^4$ (HeLa and derivatives), or $2 \times 10^5$ (HT1080 and derivatives) cells per 60-mm plate as described in Freedman et al., *Proc. Natl. Acad. Sci. USA* 72:4435–4439 (1972) and Tucker et al., *Cancer Res.* 37:1571–1579 (1977), which are incorporated herein by reference, and stained, after a 14- to 17-day incubation with p-iodonitrotetrazolium violet (0.5 mg/ml) for 16 h.

Cells were injected into 4- to 5-week old athymic nude mice (Harian-Sprague-Dawley) in 0.25 ml of phosphate-buffered saline at the indicated cell number. Nine mice were injected per cell line, and tumors were dissected at the indicated incubation times.

Confluent cultures of cell lines (containing $2 \times 10^6$ cells) were labeled for 5 hours in 35-mm wells with 0.4 mCi (1 Ci=37 GBq) of [$^{35}$S] methionine (Tran$^{35}$S-label, ICN) in methionine-free Dulbecco's modified Eagle's medium containing 5% (vol/vol) dialyzed fetal calf serum. Cells were washed twice in phosphate-buffered saline and scraped into 1.0 ml of RIPA-1 [50 mM Tris-HCl, pH 7.5/0.1% Nonidet P-40/250 mM NaCl/aprotinin (10 μg/ml) leupeptin (5 μg/ml) 1 mM phenylmethylsulfonyl fluoride/5 mM EDTA/soybean trypsin inhibitor (10 μg/ml)]. After addition of bovine serum albumin to 0.5 mg/ml, lysates were preabsorbed with 100 μl of a 50% (wt/vol) protein A-Sepharose (Pharmacia) slurry (prepared in RIPA-1 containing bovine serum albumin at 0.5 mg/ml) by mixing at 4° C. for 30 min and centrifuging for 10 min at 14,000 rpm in an Eppendorf microcentrifuge and 0.5-ml samples were then incubated with 1.5 pg of anti-E1A monoclonal antibody M73 (12) or control antibody [anti-fos Ab-1 (Oncogene Sciences, Mineola, N.Y.)] for 2 h at 0° C. Then 25 μl of 50% protein A-Sepharose slurry was added and the tubes were mixed for 20 min at 4° C. followed by a 2-min centrifugation and five 0.5-ml washes with RIPA-1. Pellets were then resuspended in 60 μl of sample buffer and analyzed with SDS/PAGE.

EXAMPLE II

Reverse Transformation of Malignant Cells

Figure 1A:
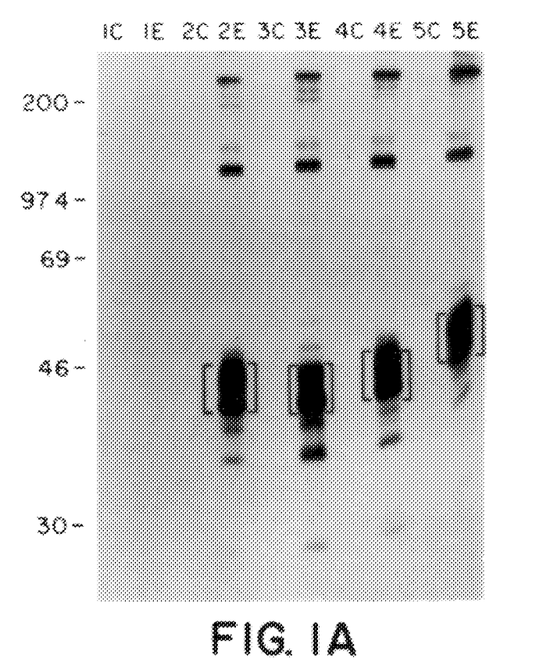
FIG. 1. Demonstration that E1A can be stably expressed in transfected tumor cells. Immunoprecipitation of E1A proteins from stably transfected and parental cell lines. [35S]Methionine-labeled proteins from E1A-expressing clones derived from HT1080 cells (lanes 1–5), HeLa cells (lanes 6–8), or A2058 cells (lanes 9–11) were immunoprecipitated with anti-E1A antibodies (E) or control antibodies (C). Lanes: 1–5, HT1080, p2AHT2a, p1Aneo3, p1Aneo15, and p1Aneo16, respectively: 6–8, HeLa, Medg18, and Medg28, respectively: 9–11, A2058, 1A58c8-1, and 1A58c11-1, respectively. The bands corresponding to E1A protein species are bracketed.
Figure 1B:
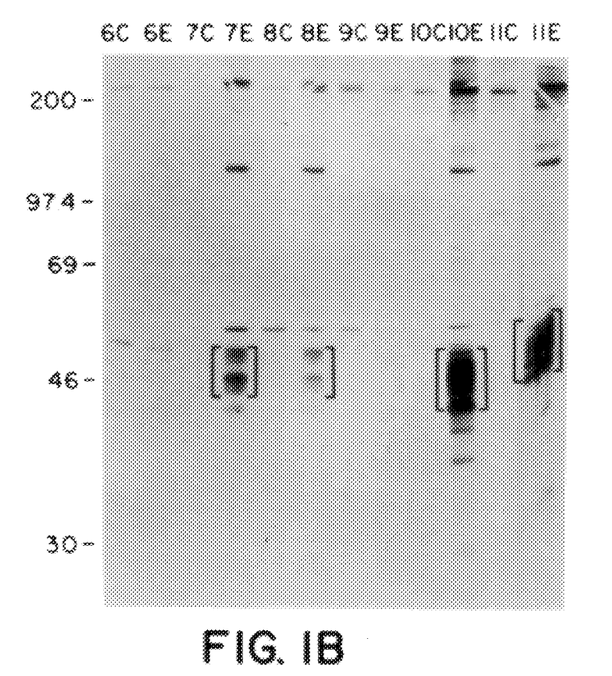

The expression of the E1A gene was documented at the RNA level by Northern blot analysis as described in Frisch et al., *Oncogene* 5:75–83 (1990) and Brunet and Berk, *Mol. Cell. Biol.* 8:4799–4807 (1988), which are incorporated herein by reference and, in the present study, protein expression was documented by immunoprecipitation with E1A-specific monoclonal antibodies (FIG. 1). Multiple species of E1A protein were detected on the gel.

Figure 2:
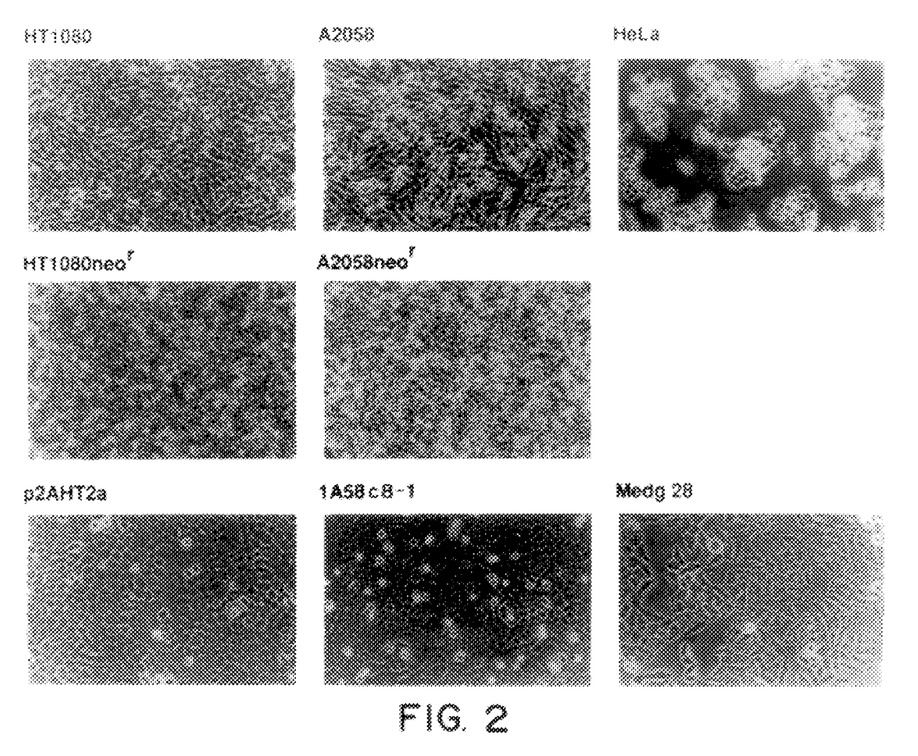
FIG. 2. Demonstration that E1A expressing cells are converted into a flat, contact-inhibited morphology. Phase-contrast micrographs of parental (top row), neomycin-resistance transfected (middle row), and E1A-expressing (bottom row) human tumor cells. Bottom row, photomicrographs of HT1080neo$^r$ and E1A-expressing HT1080 soft agarose colonies.

In each case, the E1A-transfected cells are relatively flat and "epithelioid" compared with the respective parental cell lines or lines transfected with the aph gene alone (FIG. 2A). These morphologic changes are consistent with the widely reported observation that transformed cells tend to be more refractile and less substrate-attached than normal cells as described in Edelman and Yahara, *Proc. Natl. Acad. Sci. USA* 73:2047–2051 (1976). The altered morphology was observed at the time the colonies were first identified on the G418-selection plates, suggesting that secondary stochastic changes in the genome are not required for induction of the altered phenotype.

TABLE 1

Tumorigenicity of parental tumor cells (HT1080, A2058, and HeLa) and E1A derivatives in nude mice

| Cell line | Cells injected, no. | Incubation time, days | Average tumor mass, g | SD |
|---|---|---|---|---|
| HT1080 | $6 \times 10^6$ | 17 | 2.2 | 0.62 |
| p2AHT2a | $6 \times 10^6$ | 17 | 0.04 | 0.04 |
| HT1080 | $2 \times 10^6$ | 17 | 1.2 | 0.3 |
| p1Aneo15 | $2 \times 10^6$ | 17 | 0.25 | 0.3 |
| p1Aneo16 | $2 \times 10^6$ | 17 | 0.0 | 0 |
| A2058 | $1 \times 10^7$ | 18 | 1.2 | 0.3 |
| 1A58c8-1 | $1 \times 10^7$ | 18 | 0.0 | 0 |
| 1A58c11-1 | $1 \times 10^7$ | 18 | 0.0 | 0 |
| HeLa | $1 \times 10^6$ | 15 | 0.4 | 0.1 |
| Medg 28 | $1 \times 10^6$ | 15 | 0.1 | 0.03 |

Figure 3:
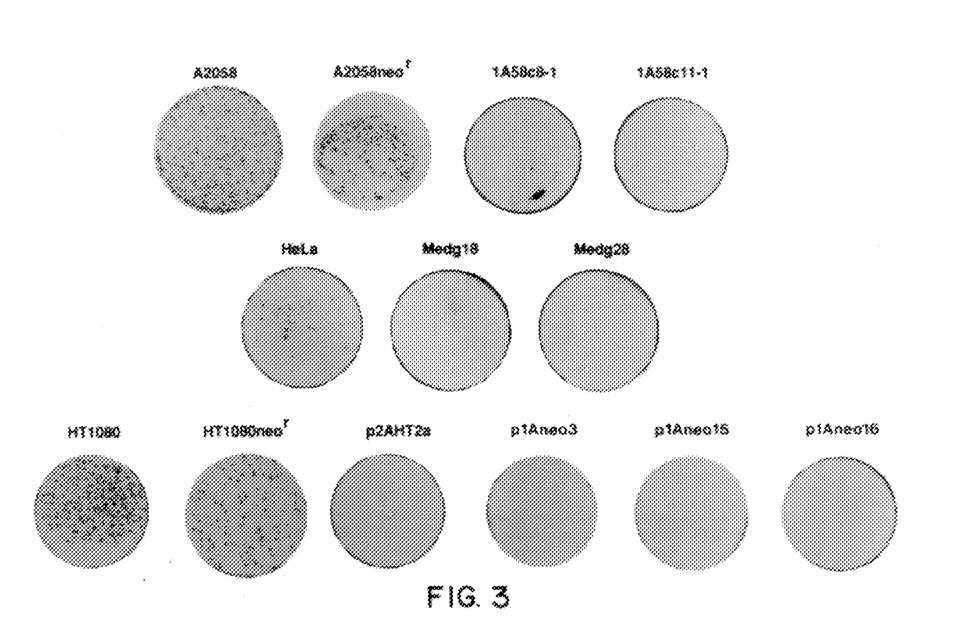
FIG. 3. Demonstration that E1A expression causes loss of anchorage-independent growth (soft agarose colony formation) in transfected tumor cells. Soft agarose colony formation assays of parental neomycin-resistance transfected, and E1A-expressing human tumor cells.

The tumorigenicity of cells in vivo generally correlated with their ability to form anchorage-independent colonies (Shin et al., *Proc. Natl. Acad. Sci. USA* 72:4435–4439 (1972) and Tucker et al., *Cancer Res.* 37:1571–1579 (1977), which are hereby incorporated by reference). To test for anchorage-independent growth, cell lines were plated in soft agarose at fixed cell number and monitored for colony formation. While the parental tumor cell lines formed colonies in soft agarose (=1% efficiency), E1A-expressing clones derived from these cell lines failed to form colonies (FIG. 3). In fact, microscopic examination revealed that the E1A-expressing clones failed even to initiate colony formation on soft agarose, ruling out a growth-rate effect. The colony-suppressed phenotype was never observed among 15 independent HT1080 clones that had been transfected with the aph gene alone and selected for G418 resistance; these results indicate that the soft agarose colony suppression was an effect of the E1A gene and not of the selection process. These observations demonstrate that E1A expression can convert the human tumor cells to a phenotype that is anchorage-dependent for growth.

Figure 4:
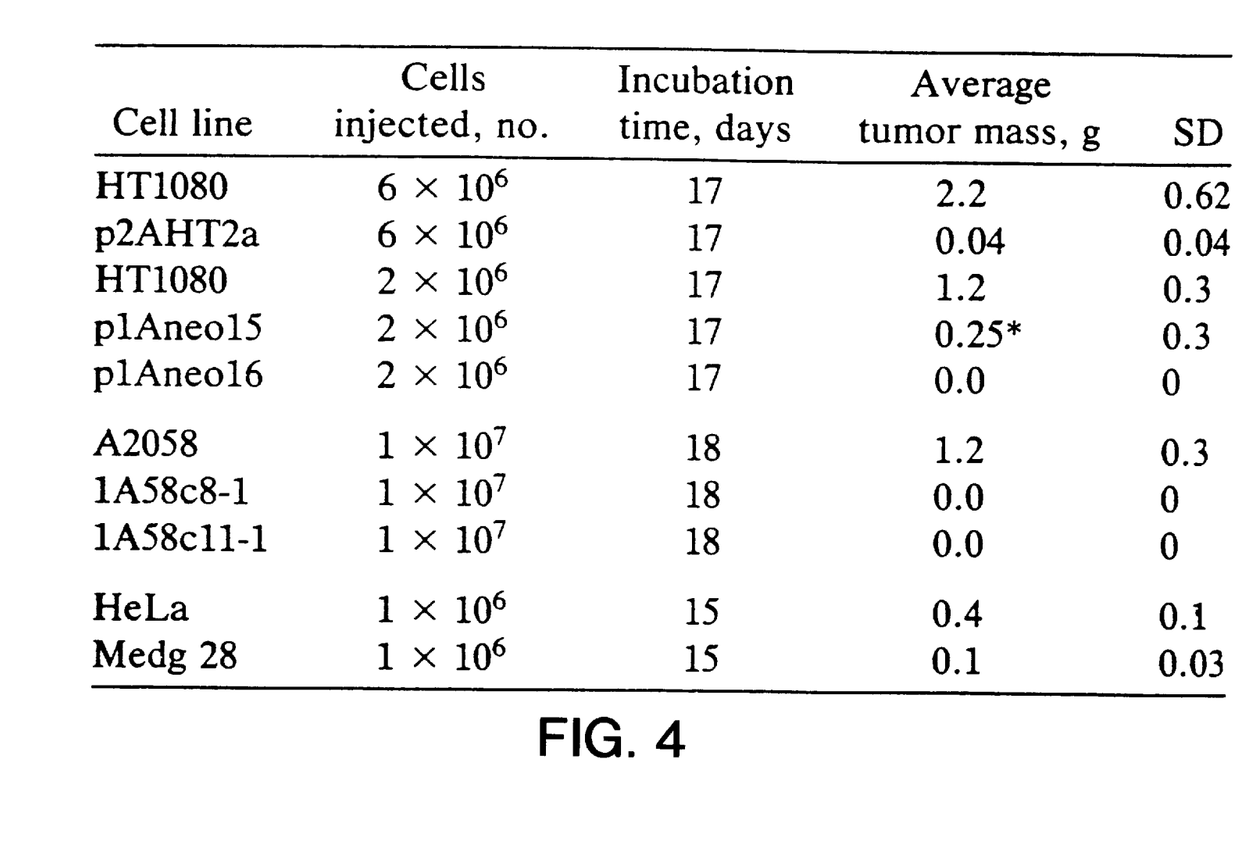
FIG. 4. Demonstration that E1A reduces tumorigenicity of human tumor cells. Tumorigenicity of parental tumor cells (HT1080, A2058, and HeLa) and E1A derivatives in nude mice.

To test whether E1A expression rendered the human tumor cell lines non-tumorigenic in vivo, they were injected subcutaneously into nude athymic mice and monitored for tumor formation (FIG. 4). The parental cell lines formed large tumors with incubation times of 15–17 days. In contrast, the E1A-expressing A2058 and HT1080 cells produced undetectable or very small tumors. E1A only partially suppressed tumorigenicity in the HeLa cells (4-fold), possibly because transcription from the glucocorticoid-dependent murine mammary tumor virus promoter, which was driving the E1A gene, was compromised in the subcutaneous environment.

To further rule out the possibility that E1A simply slowed growth rates so as to render soft agar colonies and tumors undetectable at short time points, growth curves were constructed. E1A did not substantially affect the growth rate of subconfluent tumor cells.

The possibility that the tumor suppression could have been augmented by the ability of E1A to sensitize certain cells to lysis by tumor necrosis factor α was also considered. This was, however, unlikely in that $^{51}$Cr-labeled p2AHT2a cells gave only 18% more lysis than parental HT1080 cells in tumor necrosis factor α at 500 units/ml—a dose high enough to kill nearly 100% of sensitive rodent cells.

This is the first time that the phenotypic effects of E1A in human cells have been described. The experiments reported here establish that E1A converts three diverse types of human tumor cells into a phenotypically non-transformed state. Paradoxically, a salient phenotypic effect of adenovirus E1A is collaboration with the ras oncogene to transform primary rodent cells. Since specific rodent cell types can turn out to be affected antioncogenically by E1A, it would be premature to ascribe this discrepancy to species differences only, especially since the effects of E1A expression in spontaneously transformed rodent cell lines have not been reported.

EXAMPLE III

Inhibition of Tumor Cell Growth By Contact Inhibition

This example describes a method for inhibiting the uncontrolled replication of human tumor cells through contact inhibition with cells reverse transformed by E1A expression.

Figure 6:
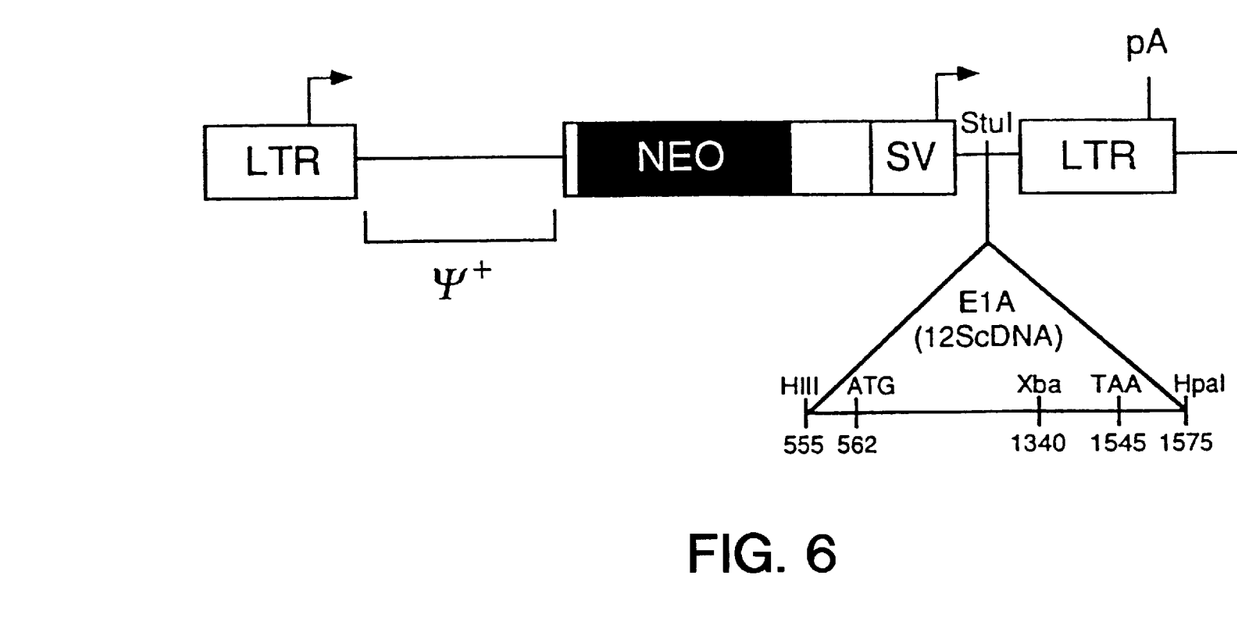
FIG. 6. Structure of a reverse-transforming retrovirus construct. The 243 amino acid form of E1A (12S cDNA) was cut at adenovirus map position 610 with BstX1 and the 5' end was reconstructed with a double-stranded oligonucleotide, thus removing all E1A 5' noncoding sequences. The HindIII end of this oligonucleotide was made blunt ended and the 3' end of E1A was cut with HpaI (map position 1575) to remove the polyA addition site. The resulting E1A sequence was subcloned into the retrovirus vector LNSX (described in Miller and Rosman, *Biotechniques* 7:980–990 (1989). Retroviruses were then packaged as described in the text.

Construction of E1A viral expression vectors was achieved by subcloning cDNAs encoding the 243 amino acid or 289 amino acid E1A proteins of adenovirus type 5 into the retroviral vectors: LNCX, LNSX. (For vector descriptions, see Miller and Rosman, *Biotechniques* 7:980–990 (1989); details of plasmid constructions are given in the legend to FIG. 6). 10 μg of these plasmid DNAs were transfected as in Example II into the ecotropic packaging cell line gpE86 (maintained in hygromycin/mycophenolic acid selection medium). At 48 h post transfection, unselected virus stocks were prepared by collecting conditioned media, clearing by centrifugation and freezing. These viral stocks were used to infect the amphotropic packaging cell line gpEam12 (cells available from ATCC) in 35 mm wells by incubation for 12 h in DME/10% fetal calf serum media containing 4 μg/ml polybrene. At 24 h post-infection, cells were split at ratios between 1:100–1:300, and infected cells were selected in 500 μg/ml G418 for 3 weeks. Virus-producing cell lines were expanded into 35 mm wells and conditioned media containing virus was prepared for each line. Virus stocks were prepared from producer cell lines containing either 243 amino acid E1A or 289 amino acid E1A, in the vectors LNCX and LNSX (which promote transcription using internal CMV or SV40 early enhancers, respectively).

These stocks were used to infect the human fibrosarcoma line HT1080 by incubating 0.4 ml of virus stock with a 35 mm well of HT1080 cells for 8 h in medium containing polybrene; infected cells were split at various ratios 24 h post-infection, and either G418-resistant clones or mixed populations of infected cells were analyzed further.

The results were as follows. In cultures infected with some of the virus stocks, no morphologic change was observed compared with the uninfected controls. Western blotting demonstrated that these infected cultures were negative for E1A expression, possibly as a result of rearrangement of retroviral DNA sequences in the producer cell lines.

With one of the virus stocks, encoding the 243 amino acid form of E1A in the LNSX vector (especially 4/LNSX8), essentially 100% of the cells were converted into a morphology closely resembling that of E1A-transfected cells (see FIG. 2). Upon prolonged incubation, these cells maintained their epithelioid morphology and failed to grow beyond monolayer stage, suggesting contact inhibition of growth. These cells expressed an amount of E1A protein per cell comparable with the levels seen in calcium phosphate-transfected cell lines, but all of this E1A was the 243 amino acid form, as expected.

With other virus stocks, a mixture of "transformed morphology" and "E1A morphology" clones was noted after G418 selection. Significantly, upon longer incubation, these cultures were found to eventually (2–3 weeks post-infection) convert into nearly 100% "E1A morphology"; i.e., epithelioid, contact-inhibited cells.

The latter phenomenon indicates that cells expressing E1A contact-inhibit each other. They also contact-inhibit tumor cells. Consistant with this observation is that the tumor cells are incapable of "sending" contact inhibition signals as expected, but are capable of "receiving" and responding to them. These differential signaling responses eventually produce the outcome described in the preceding paragraph. Thus, contact inhibition can be achieved within an hyperproliferating cell population by expressing E1A in a fraction of the cells and not within the total population.

The conceptual advance bearing important ramifications for cancer therapy is as follows. Genes or drugs targeted to kill tumor cells are effective in eradicating tumors only if 100% of the cells are exposed to the drug or forced to express the gene. This condition is seldom, if ever, satisfied in vivo. E1A-expressing cells can dominantly prevent the growth of neighboring tumor cells, so forcing a small fraction of the cells in a tumor to express E1A will to eradicate the tumor. Delivery of E1A by retroviral vectors will achieve this effect. E1A is unique among tumor suppressor genes presently characterized in preserving the viability of the cells into which it is introduced, and this property can be exploited to eradicate tumor growth.

Although the invention has been described with reference to the disclosed embodiments, those skilled in the art will readily appreciate that the specific experiments detailed are only illustrative of the invention. It should be understood that various modifications can be made without departing from the spirit of the invention. Accordingly, the invention is limited only by the following claims.

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:

( A ) LENGTH: 1000 base pairs
( B ) TYPE: nucleic acid
( C ) STRANDEDNESS: both
( D ) TOPOLOGY: linear ( i i ) MOLECULE TYPE: cDNA ( i i i ) HYPOTHETICAL: NO ( i v ) ANTI-SENSE: NO ( i x ) FEATURE:
( A ) NAME/KEY: CDS
( B ) LOCATION: join(10..426, 681..993)
( D ) OTHER INFORMATION: /note= "This protein is the product
of alternative splicing of the precursor RNA such
that protein in this form is a subset of the larger
E1A protein as shown in SEQ ID NOS: 3-4."

( x i ) SEQUENCE DESCRIPTION: SEQ ID NO:1:

```
GGACTGAAA ATG AGA CAT ATT ATC TGC CAC GGA GGT GTT ATT ACC GAA              48
          Met Arg His Ile Ile Cys His Gly Gly Val Ile Thr Glu
           1               5                  10

GAA ATG GCC GCC AGT CTT TTG GAC CAG CTG ATC GAA GAG GTA CTG GCT            96
Glu Met Ala Ala Ser Leu Leu Asp Gln Leu Ile Glu Glu Val Leu Ala
        15                  20                  25

GAT AAT CTT CCA CCT CCT AGC CAT TTT GAA CCA CCT ACC CTT CAC GAA           144
Asp Asn Leu Pro Pro Pro Ser His Phe Glu Pro Pro Thr Leu His Glu
 30                  35                  40                  45

CTG TAT GAT TTA GAC GTG ACG GCC CCC GAA GAT CCC AAC GAG GAG GCG           192
Leu Tyr Asp Leu Asp Val Thr Ala Pro Glu Asp Pro Asn Glu Glu Ala
                 50                  55                  60

GTT TCG CAG ATT TTT CCC GAC TCT GTA ATG TTG GCG GTG CAG GAA GGG           240
Val Ser Gln Ile Phe Pro Asp Ser Val Met Leu Ala Val Gln Glu Gly
             65                  70                  75

ATT GAC TTA CTC ACT TTT CCG CCG GCG CCC GGT TCT CCG GAG CCG CCT           288
Ile Asp Leu Leu Thr Phe Pro Pro Ala Pro Gly Ser Pro Glu Pro Pro
         80                  85                  90

CAC CTT TCC CGG CAG CCC GAG CAG CCG GAG CAG AGA GCC TTG GGT CCG           336
His Leu Ser Arg Gln Pro Glu Gln Pro Glu Gln Arg Ala Leu Gly Pro
     95                 100                 105

GTT TCT ATG CCA AAC CTT GTA CCG GAG GTG ATC GAT CTT ACC TGC CAC           384
Val Ser Met Pro Asn Leu Val Pro Glu Val Ile Asp Leu Thr Cys His
110                 115                 120                 125

GAG GCT GGC TTT CCA CCC AGT GAC GAC GAG GAT GAA GAG GGT                   426
Glu Ala Gly Phe Pro Pro Ser Asp Asp Glu Asp Glu Glu Gly
                130                 135

GAGGAGTTTG TGTTAGATTA TGTGGAGCAC CCCGGGCACG GTTGCAGGTC TTGTCATTAT         486

CACCGGAGGA ATACGGGGGA CCCAGATATT ATGTGTTCGC TTTGCTATAT GAGGACCTGT         546

GGCATGTTTG TCTACAGTAA GTGAAAATTA TGGGCAGTGG GTGATAGAGT GGTGGGTTTG         606

GTGTGGTAAT TTTTTTTTA ATTTTACAG TTTTGTGGTT TAAAGAATTT TGTATTGTGA           666

TTTTTTTAAA AGGT CCT GTG TCT GAA CCT GAG CCT GAG CCC GAG CCA GAA           716
               Pro Val Ser Glu Pro Glu Pro Glu Pro Glu Pro Glu
               140                 145                 150

CCG GAG CCT GCA AGA CCT ACC CGC CGT CCT AAA ATG GCG CCT GCT ATC           764
Pro Glu Pro Ala Arg Pro Thr Arg Arg Pro Lys Met Ala Pro Ala Ile
                155                 160                 165

CTG AGA CGC CCG ACA TCA CCT GTG TCT AGA GAA TGC AAT AGT AGT ACG           812
Leu Arg Arg Pro Thr Ser Pro Val Ser Arg Glu Cys Asn Ser Ser Thr
        170                 175                 180

GAT AGC TGT GAC TCC GGT CCT TCT AAC ACA CCT CCT GAG ATA CAC CCG           860
Asp Ser Cys Asp Ser Gly Pro Ser Asn Thr Pro Pro Glu Ile His Pro
    185                 190                 195
```

| | | | | | | | | | | | | | | | | |
|---|---|---|---|---|---|---|---|---|---|---|---|---|---|---|---|---|
| GTG | GTC | CCG | CTG | TGC | CCC | ATT | AAA | CCA | GTT | GCC | GTG | AGA | GTT | GGT | GGG | 908 |
| Val | Val | Pro | Leu | Cys | Pro | Ile | Lys | Pro | Val | Ala | Val | Arg | Val | Gly | Gly | |
| 200 | | | | | 205 | | | | | 210 | | | | | 215 | |
| CGT | CGC | CAG | GCT | GTG | GAA | TGT | ATC | GAG | GAC | TTG | CTT | AAC | GAG | CCT | GGG | 956 |
| Arg | Arg | Gln | Ala | Val | Glu | Cys | Ile | Glu | Asp | Leu | Leu | Asn | Glu | Pro | Gly | |
| | | | | 220 | | | | | 225 | | | | | 230 | | |
| CAA | CCT | TTG | GAC | TTG | AGC | TGT | AAA | CGC | CCC | AGG | CCATAAGGTG | T | | | | 1000 |
| Gln | Pro | Leu | Asp | Leu | Ser | Cys | Lys | Arg | Pro | Arg | Pro | | | | | |
| | | | 235 | | | | | 240 | | | | | | | | |

( 2 ) INFORMATION FOR SEQ ID NO:2:

( i ) SEQUENCE CHARACTERISTICS:
        ( A ) LENGTH: 243 amino acids
        ( B ) TYPE: amino acid
        ( D ) TOPOLOGY: linear     ( i i ) MOLECULE TYPE: protein     ( x i ) SEQUENCE DESCRIPTION: SEQ ID NO:2:

| | | | | | | | | | | | | | | |
|---|---|---|---|---|---|---|---|---|---|---|---|---|---|---|
| Met | Arg | His | Ile | Ile | Cys | His | Gly | Gly | Val | Ile | Thr | Glu | Glu | Met | Ala |
| 1 | | | | 5 | | | | | 10 | | | | | 15 | |
| Ala | Ser | Leu | Leu | Asp | Gln | Leu | Ile | Glu | Val | Leu | Ala | Asp | Asn | Leu | |
| | | | 20 | | | | | 25 | | | | | 30 | | |
| Pro | Pro | Pro | Ser | His | Phe | Glu | Pro | Thr | Leu | His | Glu | Leu | Tyr | Asp | |
| | | | 35 | | | | | 40 | | | | | 45 | | |
| Leu | Asp | Val | Thr | Ala | Pro | Glu | Asp | Pro | Asn | Glu | Glu | Ala | Val | Ser | Gln |
| | | 50 | | | | | 55 | | | | | 60 | | | |
| Ile | Phe | Pro | Asp | Ser | Val | Met | Leu | Ala | Val | Gln | Glu | Gly | Ile | Asp | Leu |
| 65 | | | | | 70 | | | | | 75 | | | | | 80 |
| Leu | Thr | Phe | Pro | Pro | Ala | Pro | Gly | Ser | Pro | Glu | Pro | Pro | His | Leu | Ser |
| | | | | 85 | | | | | 90 | | | | | 95 | |
| Arg | Gln | Pro | Glu | Gln | Pro | Glu | Gln | Arg | Ala | Leu | Gly | Pro | Val | Ser | Met |
| | | | | 100 | | | | | 105 | | | | | 110 | |
| Pro | Asn | Leu | Val | Pro | Glu | Val | Ile | Asp | Leu | Thr | Cys | His | Glu | Ala | Gly |
| | | | 115 | | | | | 120 | | | | | 125 | | |
| Phe | Pro | Pro | Ser | Asp | Asp | Glu | Asp | Glu | Glu | Gly | Pro | Val | Ser | Glu | Pro |
| | 130 | | | | | 135 | | | | | 140 | | | | |
| Glu | Pro | Glu | Pro | Glu | Pro | Glu | Pro | Glu | Pro | Ala | Arg | Pro | Thr | Arg | Arg |
| 145 | | | | | 150 | | | | | 155 | | | | | 160 |
| Pro | Lys | Met | Ala | Pro | Ala | Ile | Leu | Arg | Arg | Pro | Thr | Ser | Pro | Val | Ser |
| | | | | 165 | | | | | 170 | | | | | 175 | |
| Arg | Glu | Cys | Asn | Ser | Ser | Thr | Asp | Ser | Cys | Asp | Ser | Gly | Pro | Ser | Asn |
| | | | 180 | | | | | 185 | | | | | 190 | | |
| Thr | Pro | Pro | Glu | Ile | His | Pro | Val | Val | Pro | Leu | Cys | Pro | Ile | Lys | Pro |
| | | 195 | | | | | 200 | | | | | 205 | | | |
| Val | Ala | Val | Arg | Val | Gly | Gly | Arg | Arg | Gln | Ala | Val | Glu | Cys | Ile | Glu |
| | 210 | | | | | 215 | | | | | 220 | | | | |
| Asp | Leu | Leu | Asn | Glu | Pro | Gly | Gln | Pro | Leu | Asp | Leu | Ser | Cys | Lys | Arg |
| 225 | | | | | 230 | | | | | 235 | | | | | 240 |
| Pro | Arg | Pro | | | | | | | | | | | | | |

( 2 ) INFORMATION FOR SEQ ID NO:3:

( i ) SEQUENCE CHARACTERISTICS:
        ( A ) LENGTH: 1000 base pairs
        ( B ) TYPE: nucleic acid
        ( C ) STRANDEDNESS: both
        ( D ) TOPOLOGY: linear ( i i ) MOLECULE TYPE: cDNA ( i x ) FEATURE:
    ( A ) NAME/KEY: CDS
    ( B ) LOCATION: join(10..564, 681..993)

( x i ) SEQUENCE DESCRIPTION: SEQ ID NO:3:

```
GGACTGAAA ATG AGA CAT ATT ATC TGC CAC GGA GGT GTT ATT ACC GAA           48
          Met Arg His Ile Ile Cys His Gly Gly Val Ile Thr Glu
           1               5                  10

GAA ATG GCC GCC AGT CTT TTG GAC CAG CTG ATC GAA GAG GTA CTG GCT          96
Glu Met Ala Ala Ser Leu Leu Asp Gln Leu Ile Glu Glu Val Leu Ala
         15                  20                  25

GAT AAT CTT CCA CCT CCT AGC CAT TTT GAA CCA CCT ACC CTT CAC GAA         144
Asp Asn Leu Pro Pro Pro Ser His Phe Glu Pro Pro Thr Leu His Glu
 30                  35                  40                  45

CTG TAT GAT TTA GAC GTG ACG GCC CCC GAA GAT CCC AAC GAG GAG GCG         192
Leu Tyr Asp Leu Asp Val Thr Ala Pro Glu Asp Pro Asn Glu Glu Ala
                 50                  55                  60

GTT TCG CAG ATT TTT CCC GAC TCT GTA ATG TTG GCG GTG CAG GAA GGG         240
Val Ser Gln Ile Phe Pro Asp Ser Val Met Leu Ala Val Gln Glu Gly
             65                  70                  75

ATT GAC TTA CTC ACT TTT CCG CCG GCG CCC GGT TCT CCG GAG CCG CCT         288
Ile Asp Leu Leu Thr Phe Pro Pro Ala Pro Gly Ser Pro Glu Pro Pro
         80                  85                  90

CAC CTT TCC CGG CAG CCC GAG CAG CCG GAG CAG AGA GCC TTG GGT CCG         336
His Leu Ser Arg Gln Pro Glu Gln Pro Glu Gln Arg Ala Leu Gly Pro
     95                 100                 105

GTT TCT ATG CCA AAC CTT GTA CCG GAG GTG ATC GAT CTT ACC TGC CAC         384
Val Ser Met Pro Asn Leu Val Pro Glu Val Ile Asp Leu Thr Cys His
110                 115                 120                 125

GAG GCT GGC TTT CCA CCC AGT GAC GAC GAG GAT GAA GAG GGT GAG GAG         432
Glu Ala Gly Phe Pro Pro Ser Asp Asp Glu Asp Glu Glu Gly Glu Glu
                130                 135                 140

TTT GTG TTA GAT TAT GTG GAG CAC CCC GGG CAC GGT TGC AGG TCT TGT         480
Phe Val Leu Asp Tyr Val Glu His Pro Gly His Gly Cys Arg Ser Cys
            145                 150                 155

CAT TAT CAC CGG AGG AAT ACG GGG GAC CCA GAT ATT ATG TGT TCG CTT         528
His Tyr His Arg Arg Asn Thr Gly Asp Pro Asp Ile Met Cys Ser Leu
        160                 165                 170

TGC TAT ATG AGG ACC TGT GGC ATG TTT GTC TAC AGT AAGTGAAAAT              574
Cys Tyr Met Arg Thr Cys Gly Met Phe Val Tyr Ser
175                 180                 185

TATGGGCAGT GGGTGATAGA GTGGTGGGTT TGGTGTGGTA ATTTTTTTT TAATTTTTAC        634

AGTTTTGTGG TTTAAAGAAT TTTGTATTGT GATTTTTTA AAAGGT CCT GTG TCT          689
                                                 Pro Val Ser

GAA CCT GAG CCT GAG CCC GAG CCA GAA CCG GAG CCT GCA AGA CCT ACC         737
Glu Pro Glu Pro Glu Pro Glu Pro Glu Pro Ala Arg Pro Thr
190                 195                 200

CGC CGT CCT AAA ATG GCG CCT GCT ATC CTG AGA CGC CCG ACA TCA CCT         785
Arg Arg Pro Lys Met Ala Pro Ala Ile Leu Arg Arg Pro Thr Ser Pro
205                 210                 215                 220

GTG TCT AGA GAA TGC AAT AGT AGT ACG GAT AGC TGT GAC TCC GGT CCT         833
Val Ser Arg Glu Cys Asn Ser Ser Thr Asp Ser Cys Asp Ser Gly Pro
                225                 230                 235

TCT AAC ACA CCT CCT GAG ATA CAC CCG GTG GTC CCG CTG TGC CCC ATT         881
Ser Asn Thr Pro Pro Glu Ile His Pro Val Val Pro Leu Cys Pro Ile
            240                 245                 250

AAA CCA GTT GCC GTG AGA GTT GGT GGG CGT CGC CAG GCT GTG GAA TGT         929
Lys Pro Val Ala Val Arg Val Gly Gly Arg Arg Gln Ala Val Glu Cys
```

```
                      255                       260                         265
ATC  GAG  GAC  TTG  CTT  AAC  GAG  CCT  GGG  CAA  CCT  TTG  GAC  TTG  AGC  TGT      977
Ile  Glu  Asp  Leu  Leu  Asn  Glu  Pro  Gly  Gln  Pro  Leu  Asp  Leu  Ser  Cys
     270                      275                      280

AAA  CGC  CCC  AGG  CCATAAGGTG  T                                                   1000
Lys  Arg  Pro  Arg  Pro
285
```

( 2 ) INFORMATION FOR SEQ ID NO:4:

( i ) SEQUENCE CHARACTERISTICS:
        ( A ) LENGTH: 289 amino acids
        ( B ) TYPE: amino acid
        ( D ) TOPOLOGY: linear     ( i i ) MOLECULE TYPE: protein     ( x i ) SEQUENCE DESCRIPTION: SEQ ID NO:4:

```
Met  Arg  His  Ile  Ile  Cys  His  Gly  Gly  Val  Ile  Thr  Glu  Glu  Met  Ala
 1                   5                        10                       15

Ala  Ser  Leu  Leu  Asp  Gln  Leu  Ile  Glu  Val  Leu  Ala  Asp  Asn  Leu
               20                       25                  30

Pro  Pro  Pro  Ser  His  Phe  Glu  Pro  Pro  Thr  Leu  His  Glu  Leu  Tyr  Asp
               35                       40                  45

Leu  Asp  Val  Thr  Ala  Pro  Glu  Asp  Pro  Asn  Glu  Glu  Ala  Val  Ser  Gln
     50                       55                       60

Ile  Phe  Pro  Asp  Ser  Val  Met  Leu  Ala  Val  Gln  Glu  Gly  Ile  Asp  Leu
 65                      70                       75                       80

Leu  Thr  Phe  Pro  Pro  Ala  Pro  Gly  Ser  Pro  Glu  Pro  Pro  His  Leu  Ser
                    85                       90                       95

Arg  Gln  Pro  Glu  Gln  Pro  Glu  Gln  Arg  Ala  Leu  Gly  Pro  Val  Ser  Met
                    100                      105                      110

Pro  Asn  Leu  Val  Pro  Glu  Val  Ile  Asp  Leu  Thr  Cys  His  Glu  Ala  Gly
               115                      120                      125

Phe  Pro  Pro  Ser  Asp  Asp  Glu  Asp  Glu  Glu  Gly  Glu  Glu  Phe  Val  Leu
     130                      135                      140

Asp  Tyr  Val  Glu  His  Pro  Gly  His  Gly  Cys  Arg  Ser  Cys  His  Tyr  His
145                           150                      155                 160

Arg  Arg  Asn  Thr  Gly  Asp  Pro  Asp  Ile  Met  Cys  Ser  Leu  Cys  Tyr  Met
                    165                      170                      175

Arg  Thr  Cys  Gly  Met  Phe  Val  Tyr  Ser  Pro  Val  Ser  Glu  Pro  Glu  Pro
                    180                      185                      190

Glu  Pro  Glu  Pro  Glu  Pro  Glu  Pro  Ala  Arg  Pro  Thr  Arg  Arg  Pro  Lys
               195                      200                      205

Met  Ala  Pro  Ala  Ile  Leu  Arg  Arg  Pro  Thr  Ser  Pro  Val  Ser  Arg  Glu
     210                      215                      220

Cys  Asn  Ser  Ser  Thr  Asp  Ser  Cys  Asp  Ser  Gly  Pro  Ser  Asn  Thr  Pro
225                      230                      235                      240

Pro  Glu  Ile  His  Pro  Val  Val  Pro  Leu  Cys  Pro  Ile  Lys  Pro  Val  Ala
                    245                      250                      255

Val  Arg  Val  Gly  Gly  Arg  Arg  Gln  Ala  Val  Glu  Cys  Ile  Glu  Asp  Leu
               260                      265                      270

Leu  Asn  Glu  Pro  Gly  Gln  Pro  Leu  Asp  Leu  Ser  Cys  Lys  Arg  Pro  Arg
               275                      280                      285

Pro
```

I claim:

1. A method for reverse-transforming a pathologically hyperproliferative transformed human cell in a subject,
   wherein said pathologically hyperproliferative transformed cell does not overexpress the neu oncogene, comprising
   administering to the subject a nucleic acid sequence encoding E1A or a fragment or subunit of E1A having reverse-transforming activity of E1A, operatively linked to a promoter and expressing said nucleic acid sequence in said transformed cell,
   whereby said expression reverse-transforms said transformed cell such that said cell demonstrates a reduction in tumorigenic potential.

2. The method of claim 1, wherein the nucleic acid sequence encodes adenovirus E1A polypeptide.

3. The method of claim 2, wherein the E1A polypeptide is the 243 amino acid polypeptide product of the adenovirus E1A gene as shown in FIG. 5 (SEQ ID NO. 2).

4. The method of claim 1, wherein the pathologically hyperproliferative transformed human cell is a malignant cell.

5. The method of claim 1, wherein the nucleic acid sequence is in a retroviral vector.

6. The method of claim 1, wherein the pathologically hyperproliferative transformed human cell is selected from the group consisting of a sarcoma, a carcinoma, a melanoma and a breast cancer cell.

7. A method for reverse-transforming pathologically hyperproliferative transformed human cells in a tumor in a subject, wherein said pathologically hyperproliferative transformed cells do not overexpress the neu oncogene,
   comprising administering to the subject a nucleic acid sequence encoding E1A or a fragment or subunit of E1A having reverse-transforming activity of E1A, operatively linked to a promoter and expressing said nucleic acid sequence in said transformed cells,
   whereby said expression reverse-transforms said transformed cells, thereby inhibiting growth of said tumor.

8. The method of claim 7, wherein the nucleic acid sequence encodes adenovirus E1A polypeptide.

9. The method of claim 8, wherein the E1A polypeptide is the 243 amino acid polypeptide product of the adenovirus E1A gene as shown in FIG. 5 (SEQ ID NO. 2).

10. The method of claim 7, wherein the pathologically hyperproliferative transformed human cell is a malignant cell.

11. The method of claim 7, wherein the nucleic acid sequence is in a retroviral vector.

12. The method of claim 7, wherein the pathologically hyperproliferative transformed human cell is selected from the group consisting of a sarcoma, a carcinoma, a melanoma and a breast cancer cell.

* * * * *